United States Patent [19]

Jupe et al.

[11] 4,387,252

[45] Jun. 7, 1983

[54] PROCESS FOR THE PREPARATION OF POLYHYDRIC PHENOLS

[75] Inventors: Christoph Jupe, Cologne; Helmut Waldmann, Leverkusen; Hermann Seifert, Cologne, all of Fed. Rep. of Germany

[73] Assignee: Bayer Aktiengesellschaft, Leverkusen, Fed. Rep. of Germany

[21] Appl. No.: 193,572

[22] Filed: Oct. 3, 1980

[30] Foreign Application Priority Data

Oct. 19, 1979 [DE] Fed. Rep. of Germany ....... 2942366

[51] Int. Cl.$^3$ ....................... C07C 39/10; C07C 37/60
[52] U.S. Cl. ..................................... 568/771; 568/803
[58] Field of Search .............. 568/768, 771, 798, 803, 568/741

[56] References Cited

U.S. PATENT DOCUMENTS

| | | | |
|---|---|---|---|
| 3,407,237 | 10/1968 | Vesely | 568/741 |
| 3,461,170 | 8/1969 | Schmerling | 568/741 |
| 3,652,597 | 3/1972 | Bader et al. | 568/771 |
| 3,943,179 | 3/1976 | Bost et al. | 568/766 |
| 3,950,437 | 4/1976 | Imamura et al. | 568/766 |
| 4,182,918 | 1/1980 | Seifer et al. | 568/741 |

FOREIGN PATENT DOCUMENTS

| | | | |
|---|---|---|---|
| 2071464 | 9/1971 | France | 568/771 |
| 2182668 | 12/1973 | France | 568/771 |
| 2190787 | 2/1974 | France | 568/771 |
| 2201279 | 3/1974 | France | 568/771 |
| 2211434 | 7/1974 | France | 568/771 |
| 2222344 | 10/1974 | France | 568/771 |
| 2263217 | 10/1975 | France | 568/771 |
| 2318851 | 2/1977 | France | 568/771 |
| 2336364 | 7/1977 | France | 568/771 |
| 50-477934 | 4/1975 | Japan | 568/771 |
| 7312990 | 4/1974 | Netherlands | 568/771 |

OTHER PUBLICATIONS

Takamitsu et al., "Chem. Abst.", vol. 88, p. 120774u, (1978).

*Primary Examiner*—Werren B. Lone
*Attorney, Agent, or Firm*—Sprung, Horn, Kramer & Woods

[57] ABSTRACT

The invention relates to an improved process for the preparation of polyhydric phenols by hydroxylation of phenols with peroxidic hydroxylating agents and in the presence of 0.00005 to 0.03% by weight (relative to the phenols employed) of substances which can form chelate complexes with metal ions, such as nitrogen-containing di- or poly- carboxylic acids or phosphoric acid derivatives. The products of the process are known to be useful in the fields of photography, dyestuffs, plastics, fragrances and flavors.

3 Claims, No Drawings

PROCESS FOR THE PREPARATION OF POLYHYDRIC PHENOLS

The present invention relates to an improved process for the preparation of polyhydric phenols by hydroxylation of phenols.

In the hydroxylation of phenols, one or more hydroxyl groups are introduced into phenols, whereupon aromatic compounds, which possess two or more hydroxyl groups bonded directly to one or more aromatic nuclei (=polyhydric phenols), are formed. The most important polyhydric phenols are those which have two hydroxyl groups on an aromatic nucleus and are derived from phenol, naphthalene, anthracene and phenanthrene. These dihydric phenols are industrially important compounds which are produced in large quantities and are used, for example, in the fields of photography, of dyestuffs and plastics and of scents and flavour agents, and in particular as intermediate products in these fields (see, for example, Kirk-Othmer, Encyclopedia of Chemical Technology, Second Edition, Volume 11, pages 462 to 492, in particular pages 469 and 488 (1966)).

A number of processes for the preparation of polyhydric phenols are known, in which polyhydric phenols are obtained by hydroxylation of phenols. Peroxidic compounds, for example hydrogen peroxide, peroxo salts or peracids, in particular percarboxylic acids, are frequently used as the hydroxylating agent in these processes (see, for example, DE-AS (German Published Specification) No. 2,064,497, DE-AS (German Published Specification) No. 1,593,968, DE-AS (German Published Specification) No. 1,543,830, DE-AS (German Published Specification) No. 2,364,181, DE-AS (German Published Specification) No. 2,407,398, DE-OS (German Published Specification) No. 2,658,866, DE-OS (German Published Specification) No. 2,658,943, JA-OS (Japanese Laid-Open Specification) No. 54-55 530 (1979) and JA-OS (Japanese Laid-Open Specification) No. 54-66 629 (1979)). The phenols to be hydroxylated are in general employed in these processes in a large excess, relative to the peroxidic hydroxylating agent, that is to say the phenols to be hydroxylated are only partly hydroxylated. Thus, for example, DE-OS (German Published Specification) No. 1,593,968 which corresponds to U.S. Pat. No. 3,514,490, reports that the degree of conversion of the phenol employed should not exceed 30%, since otherwise the yield of polyhydric phenols, in this case diphenols, decreases very rapidly. In DE-OS (German Published Specification) No. 2,364,181, which corresponds to British Pat. Nos. 1,423,280, 1,432,780 and 1,449,447, it is reported that when peracids are used as the hydroxylating agent for phenols, it is expedient to employ not more than 0.5 mol of peracid per mol of phenol, since larger amounts of this oxidising agent effect secondary oxydation, which extremely decreases the yield of the desired product.

When such processes are carried out on an industrial scale, the unreacted portions of the phenols employed must therefore be recovered after the hydroxylation reaction and used again in the hydroxylation reaction. If appropriate, amounts of fresh phenols equivalent to the amounts which have been reacted in the hydroxylation reaction are added to the recycled phenols.

It is also known from DE-OS (German Published Specification) No. 2,364,181 that diphenols are obtained in improved yields and selectivities if the reaction of monophenols is carried out in the presence of certain peracid stabilisers or catalysts, which can have a structure from which it can be assumed, theoretically, that they can form chelate complexes with heavy metal ions. In this process, 0.05 to 1% by weight of peracid stabiliser or catalyst is required, relative to the monophenol. DE-OS (German Published Specification) No. 2,364,181 states that the desired effect is not achieved when smaller amounts of peracid stabiliser or catalyst are employed.

A process has now been found for the preparation of polyhydric phenols by hydroxylation of phenols with peroxidic hydroxylating agents with the addition of auxiliaries, which is characterised in that the hydroxylation is carried out with the addition of 0.00005 to 0.03% by weight (relative to the phenols employed) of substances which can form chelate complexes with metal ions and belong to at least one of the following groups:

carboxylic acids which have two or more carboxyl groups, contain nitrogen and can contain other substituents, and salts or esters of such acids or hydrates of such acids or hydrates of the salts of such acids;

phosphoric acid derivatives.

The carboxylic acids which contain nitrogen can contain, for example, a total of 2 to 20, preferably 6 to 14 C-atoms, 1 to 5, preferably 2 to 4 N-atoms and 2 to 5, preferably 3 to 4 carboxyl groups, it also being possible for all or some of the carboxyl groups to be present in the form of salts and/or esters; apart from carboxyl groups, said acids are preferably hydrocarbons except for cyano, amino or imino groupings.

The phosphoric acid derivatives can contain, for example, 1 to 8, perferably 2 to 6 P atoms, 0 to 50, preferably 0 to 40 C atoms and 2 to 30, preferably 2 to 25 oxygen atoms, of which at least one phosphorus atom and two oxygen atoms are part of a

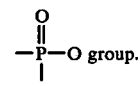
group.

Oxygen atoms which are not double bonded can be
(a) in the anionic form, for example in the form of

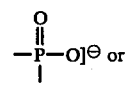 or (b) further bonded to hydrogen, $C_1$ to $C_{10}$ alkyl or phosphorus for example according to formula

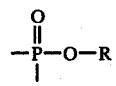

wherein R denotes hydrogen, $C_1$ to $C_{10}$ alkyl or phosphorus.

Carboxylic acids which have more than one carboxyl group and which contain one or more primary, secondary and/or tertiary amine groups in the molecule, and- /or the salts and/or the esters of such acids, or phosphoric acid derivatives with at least two

groupings are preferably employed, in the process according to the invention, as substances which can form chelate complexes with metal ions.

Carboxylic acids which have more than one carboxyl group and one or more amine groups and which are preferably employed are, for example, iminodiacetic acid, nitrilotriacetic acid, nitrilotripropionic acid, ethylenediaminetetraacetic acid, o-phenylenediaminediacetic acid, o-phenylenediaminetetraacetic acid, 1,2-cyclohexanediaminetetraacetic acid, dipicolinic acid and/or diethylenetriaminepentaacetic acid and/or salts thereof and/or esters thereof. Phosphoric acid derivatives which are preferably employed are, for example, sodium pyrophosphate ($Na_4P_2O_7$) or derivatives having the composition $Na_5R_5(P_3O_{10})_2$ (in which R=2-ethylhexyl) or oxyethanediphosphonic acid of the formula

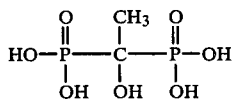

and/or salts thereof and/or esters thereof. Nitrilotriacetic acid, ethylenediaminetetraacetic acid and/or alkali metal salts and/or alkaline earth metal salts thereof and/or esters thereof are very particularly preferably employed. Within this group of substances which can form chelate complexes with metal ions, the disodium salt of ethylenediaminetetraacetic acid is again preferred. Esters of said carboxylic acids or phosphoric acids referred to above are preferably alkyl esters having 1 to 10, especially 1 to 8 carbon atoms. Salts of said carboxylic acids or phosphoric acids referred to above are preferably alkali or alkaline earth metal salts, such as sodium or potassium salts.

In general, it is entirely sufficient to use only one substance from one of the above groups of substances which form chelate complexes with metal ions in the process according to the invention. However, it is also possible to use several such substances in the process according to the invention.

The substance or substances which can form chelate complexes with metal ions are added, according to the invention, in an amount of 0.00005 to 0.03% by weight, that is to say 0.5 to 300 ppm, in each case relative to the phenols employed. This amount is preferably 5 to 200 ppm, and particularly preferably 10 to 100 ppm, in each case relative to the phenols employed.

The substances which can form chelate complexes with metal ions can be added in a pure form to the hydroxylation reaction. In this case, it should be ensured that thorough mixing takes place. These substances are preferably added to the hydroxylation reaction in dissolved form, which facilitates metering and distribution. Examples of suitable solvents are water and those solvents which are already employed in the hydroxylation reaction, as e.g. 1.2-dichloropropane, acetic acid methyl—and—ethyl ester, acetone, $C_1$ to $C_4$ monocarboxylic acid, benzene, toluene, xylene, 1.4-dioxane, 1.2-dichloroethane and 1.1.2-trichloroethane, as long as these solvents have a sufficient dissolving capacity for the substances capable of chelate formation.

The substances to be added according to the invention can be added at various points of the hydroxylation process. For example, they can be added to phenols freshly employed in the hydroxylation reaction (fresh phenols), to phenols which have not been reacted in the hydroxylation reaction and have been separated off and recycled (recycled phenols) and/or to the feed stream to the hydroxylation reaction, this stream in general consisting of fresh phenols and recycled phenols. If the fresh phenols and/or the recycled phenols are also subjected to purification or another treatment before use in the hydroxylation reaction, it is expedient for the additives according to the invention to be introduced after such a purification or treatment. The substances, which can form chelate complexes with metal ions, are preferably added before the peroxidic hydroxylating agent is introduced.

The most diverse phenols can be hydroxylated by the process according to the invention. Possible phenols are aromatic compounds which contain one or more hydroxyl groups bonded to one or more aromatic nuclei and into which one or more hydroxyl groups can be introduced using peroxidic hydroxylating agents.

It is possible for the phenols to contain no other substituents besides one or more hydroxyl groups, but they can also carry various substituents as long as these do not prevent the hydroxylation reaction taking place. Examples of possible phenols are mono-, bi- or tricyclic carbocylic hydroxy compounds which are derived from benzene, naphthalene, phenanthrene or anthracene and which still contain at least one free hydrogen atom on a ring carbon atom. In the case of phenols which are derived from benzene, a free hydrogen atom is, for example, in the 2-position or 4-position relative to a hydroxyl group which is already present. In addition to one or more hydroxyl groups the phenols can contain, for example, one or more identical or different aliphatic, cycloaliphatic, phenyl or naphthyl (preferably hydrocarbon) radicals as substituents on the aromatic nucleus or nuclei. Examples of possible aliphatic radicals are straight-chain and branched radicals with, for example, 1 to 10 C atoms, such as methyl, ethyl, isopropyl, n-butyl, i-butyl, tert.-butyl, n-pentyl, 2-methylbutyl, 3-methylbutyl, 2-ethylpropyl, n-hexyl, 2-methylpentyl, 3-methylpentyl, 4-methylpentyl, n-heptyl, n-octyl, 2-ethylhexyl, n-nonyl, 2-ethylheptyl and n-decyl. Examples of possible cycloaliphatic radicals are those with 3 to 12 C atoms, such as cyclopropyl, cyclobutyl, cyclopentyl, cyclohexyl, cycloheptyl, cyclooctyl, cyclononyl, cyclodecyl and cyclododecyl, preferably those with 5 or 6 C atoms.

In the aliphatic, cycloaliphatic, phenyl and naphthyl radicals, in each case one or more hydrogen atoms can be replaced by groups which are stable under the conditions of the hydroxylation reaction.

Examples of such groups are one or more fluorine, chlorine and/or bromine atoms; and one or more $C_1$- to $C_5$-alkoxy, $C_1$- to $C_5$-dialkylamino, carboxyl, nitro, cyano and/or sulphonic acid groups and/or carbalkoxy groups, the alkoxy radicals of which have 1 to 10 C atoms.

The aromatic nucleus or nuclei of the phenols can also be substituted by one or more of these atoms or groups.

Phenols which are derived from benzene are preferably introduced into the process according to the invention.

Examples of phenols which can be employed in the process according to the invention are those of the formula

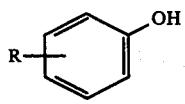
(I)

wherein R represents hydrogen, $C_1$- to $C_{10}$-alkyl, $C_3$- to $C_{12}$-cycloalkyl, phenyl, naphthyl, fluorine, chlorine, bromine or a nitro, cyano, sulphonic acid, carboxyl, carbo-$C_1$- to $C_{10}$-alkoxy, $C_1$- to $C_3$-alkoxy or $C_1$- to $C_4$-dialkylamino group, it being possible for the alkyl and cycloalkyl radicals to be substituted by fluorine, chlorine or bromine atoms or $C_1$- to $C_5$-alkoxy, $C_1$- to $C_4$-dialkylamino, carboxyl, nitro, cyano, sulphonic acid or $C_1$- to $C_{10}$-carbalkoxy groups and for the phenyl and naphthyl radicals to be substituted by fluorine, chlorine, bromine, $C_1$- to $C_{10}$-alkyl, $C_3$- to $C_{12}$-cycloalkyl or nitro, carboxyl, carbo-$C_1$- to $C_{10}$-alkoxy, $C_1$- to $C_5$-alkoxy, cyano, sulphonic acid or $C_1$- to $C_4$-dialkylamino groups.

A preferred group of phenols within the formula (I) corresponds to the phenols of the formula

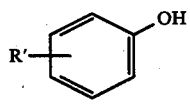
(II)

wherein R' represents hydrogen, $C_1$- to $C_3$-alkyl, $C_5$- to $C_7$-cycloalkyl, phenyl, fluorine, chlorine or a nitro, sulphonic acid, carboxyl, carbo-$C_1$- to $C_3$-alkoxy, $C_1$- to $C_2$-alkoxy or $C_1$- or $C_2$-dialkylamino group.

Monohydric phenols of the formula

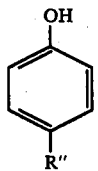
(III)

wherein R" denotes hydrogen, $C_1$- to $C_5$-alkyl, $C_5$- to $C_7$-cycloalkyl, phenyl, fluorine, chlorine, or a nitro, sulphonic acid, carboxyl, carbo-$C_1$- to $C_3$-alkoxy, $C_1$- to $C_3$-alkoxy or $C_1$- to $C_2$-dialkylamino group, are particularly preferably employed in the process according to the invention.

Specific examples which may be mentioned of phenols which are suitable for use in the process according to the invention are: phenol, o-cresol, m-cresol, p-cresol, p-cyclohexylphenol, o-cyclohexylphenol, p-phenylphenol, o-phenylphenol, m-phenylphenol, p-ethylphenol, o-ethylphenol, m-ethylphenyl, o-isopropylphenol, p-isopropylphenol, o- and p-tert.-butylphenol, p-nitrophenol, o-nitrophenol, m-nitrophenol, 2-bromo-4-methylphenol, p-chlorophenol, o-chlorophenol, m-chlorophenol, p-carbomethoxyphenol, salicylic acid ethyl ester, p-cyclopentylphenol, o-dimethylaminophenol, p-cyano-phenol, p-methoxy-phenol, o-isopropoxyphenol, p-ethoxy-phenol, 3,5-diethyl-phenol, thymol, phenol, carvacrol, 1,2,3-xylenol, 1,2,4-xylenol, 1,3,2-xylenol, 1,3,4-xylenol, 1,3,5-xylenol, 1,4,2-xylenol, α-naphthol, β-naphthol 1-hydroxy-4-methylnaphthalene, 1-hydroxy-2-methylnaphthalene, 2-hydroxy-1-methylnaphthalene, 2-hydroxy-6-methylnaphthalene, 1-hydroxy-4-isopropylnaphthalene, 1-hydroxy-4-t-butylnaphthalene, 1-hydroxy-6-phenylnaphthalene, 1-hydroxy-6-methoxy-naphthalene, 1-hydroxyanthracene, and 2-hydroxy-anthracene.

Phenol ($C_6H_5OH$) is very particularly preferably employed in the process according to the invention.

The process according to the invention is suitable for the preparation of polyhydric phenols by hydroxylation of phenols with peroxidic hydroxylating agents by the most diverse methods. Apart from the addition of substances which can form chelate complexes with metal ions, these hydroxylations can be carried out in a manner which is in itself known. Possible peroxidic hydroxylating agents are compounds which contain one or more —O—O— groups, for example $H_2O_2$, peroxodisulphates, Caro's acid, alkyl or aryl hydroperoxides, diacyl peroxides, percarboxylic acids, percarbonates, perborates and adducts of $H_2O_2$, for example the urea adduct of $H_2O_2$.

The process according to the invention can be applied, for example, to the following known hydroxylations of phenols:

to the hydroxylation of phenol, substituted phenols or phenol derivatives with hydrogen peroxide in the presence of catalytic amounts of a strong acid (see DE-AS (German Published Specification) No. 2,064,497) which corresponds to U.S. Pat. No. 3,849,502).

To the hydroxylation of aromatic compounds with hydrogen peroxide in hydrofluoric acid as the reaction medium (see DE-OS (German Published Specification) No. 1,543,953 which corresponds to U.S. Pat. Nos. 3,407,237 and 3,461,170).

The process according to the invention is preferably applied to the following hydroxylation:

to the preparation of polyhydric phenols by hydroxylation of phenol with an essentially anhydrous and hydrogen peroxide-free solution of a percarboxylic acid in an organic solvent (see DE-OS (German Published Specification) No. 2,658,943 which corresponds to U.S. Pat. No. 4,182,917). The percarboxylic acid preferably contains 1 to 4 C atoms and the organic solvent is, for example, benzene, 1,2-dichloropropane or ethyl acetate.

The process according to the invention has the advantage that polyhydric phenols can be prepared with very good selectivities by hydroxylation of phenols with peroxidic hydroxylating agents. In most cases, the selectivities are better than in the proces according to DE-OS (German Published Specification) No. 2,364,181. Another advantage of the process according to the invention is that these good selectivities are achieved with the addition of smaller amounts of auxiliaries than used in the process of DE-OS (German Published Specification) No. 2,364,181.

It is to be regarded as decidedly surprising that the process according to the invention provides such good results, since, on the basis of the statements in DE-OS (German Published Specification) No. 2,364,181, it could not be expected that the addition of auxiliaries of the type described in amounts of less than 0.05% by weight (relative to the phenols employed) has an advantageous effect.

EXAMPLES

EXAMPLE 1

20 kg of phenol (commercial goods) and 150 kg of phenol which originated from the working up of phenol which had already been reacted with perpropionic acid were brought together at 60° C., under nitrogen, 200 g of a 3% strength by weight solution of the dihydrate of the disodium salt of ethylenediaminetetraacetic acid in water were added and the components were mixed thoroughly. The phenol mixture thus prepared was fed at a rate of 10 kg per hour to the first reaction vessel of a four-stage cascade of stirred kettles thermostatically controlled at 40° C. At the same time, 2.4 kg per hour of a 20% strength by weight solution of perpropionic acid in a benzene/propionic acid mixture (5 parts by weight of benzene per 1 part by weight of propionic acid) were fed to the first reaction vessel. The reaction vessels had a useful volume of 1.7 l. The reaction mixture was forced through all the vessels once by flooding the vessels, blanketing the first kettle with nitrogen and using appropriate overflow connections.

After the last kettle, the reaction mixture had a residual content of perpropionic acid of 0.03% by weight, which corresponds to a conversion of 99.2%. The content of pyrocatechol in the reaction mixture was 2.6% by weight and the hydroquinone content was 1.4% by weight, corresponding to selectivities of 55% for pyrocatechol and 30% for hydroquinone, in each case relative to the perpropionic acid reacted.

EXAMPLE 2 (comparison example, procedure according to DE-OS (German Published Specification) No. 2,364,181)

When Example 1 was repeated with the addition of 0.5% by weight, relative to the phenol, of the dihydrate of the disodium salt of ethylenediaminetetraacetic acid, the conversion of the perpropionic acid was 98.9%, the content of pyrocatechol in the reaction mixture was 2.27% by weight and the hydroquinone content was 1.31% by weight, corresponding to selectivities 48% for pyrocatechol and 28% for hydroquinone, in each case relative to the perpropionic acid reacted.

EXAMPLE 3

282.3 g of phenol (commercial goods) were weighed into a multi-necked reaction vessel and were melted under a blanket of nitrogen. 2.6 ml of a 0.1 molar solution of the disodium salt of ethylenediaminetetraacetic acid in water were added to the melt. The contents of the reaction vessel were mixed thoroughly by vigorous stirring, blanketed with nitrogen being continued and thermostatically controlled at 45° C. 14.1 g of perpropionic acid were then added dropwise from a dropping funnel in the course of 3 to 4 minutes. The perpropionic acid was in the form of a 20% strength by weight solution in a benzene/propionic acid mixture (5 parts by weight of benzene, 1 part by weight of propionic acid).

After a reaction time of 30 minutes, the conversion of perpropionic acid was determined iodometrically on a sample of the reaction mixture. The result obtained was a conversion of the perpropionic acid employed of 97%. The reaction mixture contained 2.3% by weight of pyrocatechol and 1.4% by weight of hydroquinone, corresponding to a selectivity of 82% for pyrocatechol and hydroquinone, relative to the perpropionic acid reacted.

EXAMPLE 4 (comparison example for Example 3)

Example 3 was repeated, but without the addition of the solution of the disodium salt of ethylenediaminetetraacetic acid. For the same perpropionic acid conversion, pyrocatechol was formed with a selectivity of 40% and hydroquinone was formed with a selectivity of 21%, in each case relative to the perpropionic acid reacted.

EXAMPLE 5

0,1 ml of a solution of 4 g of oxyethanediphosphonic acid disodium salt in 96 g of water was added to the melt of 94.1 g of phenol which originated from the distillative working up of phenol which had already been reacted with less than the molar amount of perpropionic acid. The mixture was then reacted with 4.7 g of perpropionic acid at 45° C. After 60 minutes, the conversion found for the perpropionic acid employed was 98%; the reaction mixture contained 2.8 g of pyrocatechol and 1.6 g of hydroquinone, corresponding to a selectivity of 50% for pyrocatechol and a selectivity of 28% for hydroquinone.

EXAMPLE 6

235 g of phenol (commercial goods) were melted in a 500 ml glass three-necked flask with a stirrer, internal thermometer and dropping funnel at 50° C., under a blanket of nitrogen, and 3 g of a 60% strength by weight aqueous perchloric acid solution and 0.06 g of phenylimidodiacetic acid were added, whilst stirring.

7 g of a 70% strength by weight aqueous hydrogen peroxide solution was added dropwise, whilst stirring and under a blanket of nitrogen, at a rate such that the temperature did not rise above 60° C.

After one hour after the end of the dropwise addition, a hydrogen peroxide content of 0.02% by weight was determined iodometrically, which corresponds to a conversion of the hydrogen peroxide employed of 99%. The content of pyrocatechol, determined by gas chromatography, was 3.3% by weight and the hydroquinone content was 1.9% by weight, corresponding to a selectivity of 51% for pyrocatechol and a selectivity of 30% for hydroquinone, in each case relative to the hydrogen peroxide reacted.

EXAMPLE 7

108.2 g of o-cresol were melted in a 250 ml glass reaction vessel with cooled walls and a stirrer, internal thermometer and dropping funnel and the melt was warmed to 60° C. 0.02 g of the phosphoric acid derivative $Na_5R_5(P_3O_{10})_2$, in which R=2-ethylhexyl, and 1.98 g of ethyl acetate were added, whilst stirring.

A solution of 6 g of perisobutyric acid in 20.5 g of ethyl acetate was added dropwise from a dropping funnel in the course of 2 minutes, during which the temperature rose to about 80° C. and fell again, as a result of thermostatic control, to 60° C.

After 90 minutes, a perisobutyric acid content of 0.58% by weight, corresponding to a conversion of the perisobutyric acid employed of 87%, was determined iodometrically.

The content, determined by gas chromatography, of 3-methylpyrocatechol was 2.2% by weight and that of 2-methylhydroquinone was 2.1% by weight, corresponding to a selectivity of 42% for the pyrocatechol derivative and of 40% for the hydroquinone derivative, in each case relative to the perisobutyric acid reacted.

EXAMPLE 8

65 g of p-chlorophenol were initially introduced into a 250 ml three-necked glass flask with a stirrer, dropping funnel and internal thermometer and were melted and warmed to 55° C.

0.015 g of the disodium salt of cyclohexane-1,2-diaminetetraacetic acid in 3 g of water were added, whilst stirring. 3.9 g of m-chloroperbenzoic acid in 21.5 g of ethyl acetate were then added dropwise, whilst stirring, at a rate such that the temperature did not rise above 60° C. After the dropwise addition had ended, the mixture was stirred at 55° C. for 2 hours; a sample of the reaction mixture then taken had, according to iodometric determination, a m-chloroperbenzoic acid content of 0.63% by weight, corresponding to a conversion of the m-chloroperbenzoic acid employed of 85%.

In the same sample, a p-chloropyrocatechol content of 1.5% by weight was determined by gas chromatography, corresponding to a selectivity of 50.5%, relative to the peracid reacted.

EXAMPLE 9

244 g of p-ethylphenol were introduced into a 1 l three-necked glass flask and were melted at 48° C. 3.5 g of a 1% strength by weight aqueous solution of the dihydrate of the disodium salt of ethylenediaminetetraacetic acid were added to the melt, whilst stirring. A solution of 8 g of perpropionic acid in a solvent mixture of 26 g of benzene and 6 g of propionic acid were slowly added dropwise, whilst stirring and under a blanket of nitrogen, at a rate such that the temperature did not rise above 50° C. After the dropwise addition had ended, the mixture was further stirred and kept at 50° C.

Two hours after the dropwise addition had ended, a perpropionic acid content of 0.17% by weight was determined iodometrically in a sample of the reaction mixture, corresponding to a conversion of the perpropionic acid employed of 94%. In the same sample, a ethyldihydroxy benzene content of 2.54% by weight was found with the aid of gas chromatography, corresponding to a selectivity of 63% for the ethyldihydroxy benzenes relative to the perpropionic acid reacted.

What is claimed is:

1. A process for the preparation of a polyhydric phenol by hydroxylation of a phenol with an essentially anhydrous and hydrogen peroxide-free solution of a percarboxylic acid in an organic solvent, characterised in that the hydroxylation is carried out with the addition of 0.00005 to 0.03% by weight (relative to the phenol employed) of one or more compounds from the group consisting of iminodiacetic acid, nitrilotriacetic acid, nitrilotripropionic acid, ethylenediaminotetraacetic acid, o-phenylenediaminodiacetic acid, o-phenylenediaminotetraacetic acid, 1,2- cyclohexanediaminotetraacetic acid, dipicolinic acid and diethylenetriaminopentaacetic acid, salts thereof and esters thereof, sodium pyrophosphate, phosphoric acid derivatives having the composition $Na_5R_5(P_3O_{10})_2$ (in which R=2-ethylhexyl) and oxyethanediphosphonic acid and salts thereof and esters thereof.

2. Process according to claim 1, characterized in that the phenol to be hydroxylated contains no substituents other than one or more hydroxyl groups.

3. Process according to claim 1, characterized in that, in addition to one or more hydroxyl groups, the phenol to be hydroxylated contains, as substituents, one or more identical or different aliphatic, cycloaliphatic, phenyl and/or naphthyl radicals on the aromatic nucleus or nuclei; one or more fluorine, chlorine and/or bromine atoms; or one or more $C_1$- to $C_5$-alkoxy, $C_1$- to $C_5$-dialkylamino, carboxyl, nitro, cyano, sulphonic acid groups and/or carbalkoxy groups, the alkoxy radicals of which have 1 to 10 C atoms.

* * * * *